United States Patent [19]

La Zonby

[11] Patent Number: 5,209,824

[45] Date of Patent: May 11, 1993

[54] GLUTARALDEHYDE PLUS DITHIOCARBAMATES FOR CONTROLLING MICROORGANISMS IN PAPER MILLS

[75] Inventor: Judy G. La Zonby, Crystal Lake, Ill.

[73] Assignee: Nalco Chemical Company, Naperville, Ill.

[21] Appl. No.: 790,994

[22] Filed: Nov. 12, 1991

[51] Int. Cl.$^5$ .............................................. D21H 21/02
[52] U.S. Cl. .................................... 162/161; 162/199
[58] Field of Search ........................ 162/161, 158, 199

[56] References Cited

PUBLICATIONS

WPI Acc No: 90-201421/27.
WPI Acc No: 90-163626/21.
WPI Acc No: 89-361679/49.
WPI Acc No: 89-060733/08.
WPI Acc No: 88-145110/21.
CC Number EP 261607.
WPI Acc No: 88-064222/10.
WPI Acc No: 88-064220/10.
WPI Acc No: 83-802437/44.

*Primary Examiner*—Peter Chin
*Attorney, Agent, or Firm*—Robert A. Miller; John G. Premo

[57] ABSTRACT

A method for controlling microorganisms in aqueous paper mill systems which comprises treating such systems with a biocidal amount of a composition comprising: Glutaraldehyde, and a biocidal active dithiocarbamate.

3 Claims, No Drawings

GLUTARALDEHYDE PLUS DITHIOCARBAMATES FOR CONTROLLING MICROORGANISMS IN PAPER MILLS

GENERAL STATEMENT OF THE INVENTION

Glutarardehyde in combination with a biocidal active dithiocarbamate provides superior microorganism control in paper mill systems.

INTRODUCTION

In pulp and paper mill systems, slime formed by microorganisms, such as spore forming bacteria *Pseudomonas aeruoinosa*, a prominent bacterial species contributing to slimes is commonly encountered. The slime becomes entrained in the paper produced causing breakouts on the paper machines with consequent work stoppages and the loss of production time. Slimes can cause unsightly blemishes in the final product which results in rejects and wasted output. These problems have resulted in the extensive utilization of biocides in pulp and paper mill systems. Materials which have enjoyed widespread use in such applications include chlorine, organo-mercurials, chlorinated phenols, organo-bromines, and various organo sulfur compounds. All of these compounds are generally useful for this purpose but each has a variety of impediments. For example, chlorination is limited both by its specific toxicity for slime-forming organisms at economic levels and by the inability of chlorine to react which results in the loss of the chlorine before its full biocidal function may be achieved. Other biocides are attended by odor problems and hazards in respect to storage, use or handling which limit their utility. To date, no one compound or type of compound has achieved a clearly established predominance in treating paper mill systems.

Economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Their effectiveness is rapidly reduced as the result of exposure to physical conditions such as temperature or association with ingredients contained by the system toward which they exhibit an affinity. This results in a restriction or elimination of their biocidal effectiveness.

The use of such biocides involves their continuous or frequent additions to paper mill systems and their additions to a plurality of points or zones in the system. The cost of the biocide and the labor cost are considerable.

In a system experiencing relatively slow flow, such as paper mill, if a biocide is added at the beginning of the system, its biocidal effect may be completely dissipated before it has reached all of the points at which its effect is needed. As a consequence, the biocide must be added at a plurality of points, and even then a gradual loss in effectiveness will be experienced between the point of addition to the system and the next point downstream.

If it were possible to provide a biocide for paper mill systems which was effective in low dosages, was long lasting and did not require feeding at multiple points in the paper making system a valuable contribution to the paper making art would be afforded.

THE INVENTION

A method for controlling microorganisms in aqueous paper mill systems which comprises treating such systems with a biocidal amount of a composition comprising:

a) Glutaraldehyde, and
b) a biocidal active dithiocarbamate and mixtures thereof;

with the weight ratio of a:b being greater than 1:10, but less than 15:1.

It is particularly effective in controlling *Pseudomanas aeruginosa* and spore forming bacteria such as *Bacillus subtilis*.

THE BIOCIDAL ACTIVE DITHIOCARBAMATES

The biocidal active dithiocarbamates may be selected from the following:

a) Sodium dimethyldithiocarbamate
b) Potassium dimethyldithiocarbamate
c) Potassium-N-hydroxymethyl-N-methyl dithiocarbamate
d) Potassium dimethyldithiocarbamate The dithiocarbamate may be used as blends. A particularly effective blend hereafter referred to as the "dithiocarbamate blend"(DTCB), has the following composition:

| | |
|---|---|
| Disodium ethylenebisdithiocarbamate | 15% by weight |
| Sodium dimethyldithiocarbamate | 15% by weight |
| Water | Balance |

DOSAGE AND RATIO OF GLUTARALDEHYDE TO DITHIOCARBAMATES

Depending on the particular mill system the dosage will vary. It may be as little as 1 part per million by weight to as much as 100 parts per million (ppm). Typical dosages are between 5-50 ppm.

The weight ratio of Glutaraldehyde to dithiocarbamate is between greater than 1:10 to not more than 15:1. The ratio is typically between 4:1 to 10:1 with 4:1 being most preferred.

EVALUATION OF THE INVENTION a) Definition of Synergism

Synergy is mathematically demonstrated by the industry-accepted method described by S. C. Kull et al. in *Applied Microbiology*, vol. 9, pages 538–541 (1961). As applied to this invention, it is as follows:

$Q_A$ = the ppm of active of Glutaraldehyde alone which produces an endpoint.

$Q_B$ = the ppm of active Carbamate alone which produces an endpoint.

$Q_a$ = the ppm of active of Glutaraldehyde, in combination, which produces an endpoint.

$Q_b$ = the ppm of active of Carbamate, in combination, which produces an endpoint.

if $\dfrac{Q_a}{Q_A} + \dfrac{Q_b}{Q_B}$ = Synergy Index

-continued if Synergy Index is: <1, it indicates synergy
= 1, it indicates additivity
>1, it indicates antagonism b) Test Procedures Ratio Determination Glutaraldehyde and DTCB mixtures with ratios ranging from 19:1 to 1:19 were prepared at concentrations of 200 ppm a.i. and used as stock solutions to prepare lower dilutions ranging from 180ppm to 20 ppm. These dilutions were dispensed into microliter wells and mixed with equal volumes of papermill furnish contaminated with naturally occurring environmental organisms. After 4 hours and 24 hours of contact, an aliquot from each well was seeded into a second microliter plate containing Tryptic Soy Broth and incubated overnight. Minimum inhibitory concentrations (MIC) of biocides were determined from the aliquotes with the lowest concentration of biocides which failed to produce growth in the second microliter plate.

Shake Flask

A 1% synthetic furnish prepared from 50% Hardwood/50% Softwood dry lap, clay titanium oxide, alum, rosin, starch and sodium phosphates, mono and dibasic, was seeded with equal amounts of *Pseudomonas aeruoinosa* ATCC#15442 and *Bacillus subtilis* W23 to a concentration of about $1 \times 10^6$ CFU/ml and enriched with 10% Glycerol-Yeast Extract Broth. To this furnish individual biocides and biocide mixtures were added in decreasing concentrations and incubated in flasks at 37° C. in an orbital shaker. At 0, 4, and 24 hours of contact, aliquots from each flask were diluted and plated on Tryptone Glucose Extract (TGE) agar to determine the total number of viable organisms remaining. An endpoint of a 2, 3, 4, or 5 $\log_{10}$ reduction in viable organisms was then selected for calculating synergy.

Minitox

A redox dye, resazurin, was added to the above described synthetic paper furnish and dispensed into a 96 well microliter plate in 0.1 ml aliquots. An equal volume of biocide diluted to 500 ppm was added to the first well in the first row and mixed thoroughly. A 0.1 ml portion of the mixed well was then transferred to the second well in the same row and thoroughly mixed. This process was repeated to the end row resulting in a serial dilution of the biocide down to a 0.125 ppm concentration. A second biocide and subsequent biocide mixtures in various ratios were similarly diluted in the remaining rows. Biologically active organisms cause the resazurin to change from purple to pink, indicating the lowest concentration of biocide that will inhibit biological function. Synergy of the mixtures was calculated as previously described.

EXAMPLE 1

A synergy study was set up to determine if the dithiocarbamate blend would be antagonistic to glutaraldehyde added at the headbox. Since the ratios of glutaraldehyde to carbamate in this situation would be heavily in favor of the glutaraldehyde, ratios of 19:1, 4:1 and 1:1 were screened on the Minitox using Alkaline Buffered Synthetic Furnish.

The initial screening of the combination showed synergy at all combinations tested. A repeat of the test gave identical results with the exception of 1 well difference in the carbamate. This one well difference was enough to cause all the combinations to appear antagonistic.

Concentrations tested ranged from 50 ppm to 0.025 ppm. An example of the synergy attained is shown below in Table 1.

TABLE 1

| Ratio Glut:Carb. | Endpoint in ppm | Synergy Index | Synergy Rating |
|---|---|---|---|
| 100:0 | 50 | | |
| 19:1 | 3.1 | 1.61 | >1 Antagonism |
| 9:1 | 0.8 | 0.81 | <1 Synergy |
| 4:1 | 0.4 | 0.81 | <1 Synergy |
| 1:1 | 0.2 | 1.00 | =1 Additivity |
| 0:100 | 0.1 | | |

Often the furnish in which the reaction occurs effects the efficacy of the biocide. The combinations were tested in a variety of furnishes with different contact times and the results are found in the attachments, Table 1A.

TABLE 1A

| Ratio Glut:Carb | | Synergy Index | Synergy Rating |
|---|---|---|---|
| | End point after 4 hours in ppm | | |
| 100:0 | 10 | | |
| 19:1 | 10 (9.5/.5) | .96 | Synergy |
| 9:1 | 10 (9/1) | .92 | Synergy |
| 4:1 | 10 (8/2) | .84 | Synergy |
| 1:1 | 10 (5/5) | .6 | Synergy |
| 1:4 | 15 (3/12) | .54 | Synergy |
| 1:9 | 30 (3/27) | .84 | Synergy |
| 0:100 | >50 | | |
| | End point after 24 hours in ppm | | |
| 100:0 | 25 | | |
| 19:1 | 25 (23.75/1.25) | .97 | Synergy |
| 9:1 | 25 (22.5/2.5) | .94 | Synergy |
| 4:1 | 25 (20/5) | .88 | Synergy |
| 1:1 | 30 (15/15) | .85 | Synergy |
| 1:4 | 50 (10/40) | 1.07 | Antagonism |
| 1:9 | >50 (6/54) | 1.3 | Antagonism |
| 1:19 | >50 (3/57) | 1.07 | Antagonism |
| 0:100 | >50 | | |

EXAMPLE 2

Other dithiocarbamates were screened in a shake flask procedure for synergy with glutaraldehyde. Potassium-N-methyldithiocarbamate and Potassium-N-hydroxomethyl-N-methyldithiocarbamate both showed synergy with glutaraldehyde in the 4:1 ratio, using neutral Buffered synthetic furnish. See attached date, Table 1B.

TABLE 1B

| Biocide (ppm a.i.) | 0 Hours | 4 Hours | 24 Hours |
|---|---|---|---|
| Glut - 50 | $6.1 \times 10^5$ | $<10^1$ | $<10^1$ |
| Glut - 25 | $7.4 \times 10^5$ | $<10^1$ | $<10^1$ |
| Glut 12.5 | $6.8 \times 10^5$ | $1.6 \times 10^2$ | $4.0 \times 10^3$ |
| Glut 6.25 | $5.8 \times 10^5$ | $3.8 \times 10^5$ | $1.4 \times 10^7$ |
| Carbamate c - 50 | $9.5 \times 10^4$ | $4.0 \times 10^5$ | $<10^1$ |
| Carbamate c - 25 | $1.6 \times 10^5$ | $5.2 \times 10^5$ | $<10^1$ |
| Carbamate c - 12.5 | $2.1 \times 10^5$ | $2.2 \times 10^5$ | $1.3 \times 10^4$ |
| Carbamate c - 6.25 | $1.4 \times 10^5$ | $3.0 \times 10^5$ | $4.6 \times 10^4$ |
| Carbamate d - 50 | $2.3 \times 10^5$ | $5.0 \times 10^5$ | $<10^1$ |
| Carbamate d - 25 | $1.8 \times 10^5$ | $4.8 \times 10^5$ | $<10^1$ |
| Carbamate d - 12.5 | $1.8 \times 10^5$ | $4.2 \times 10^5$ | $1.1 \times 10^5$ |
| Carbamate d - 6.25 | $1.9 \times 10^5$ | $3.2 \times 10^5$ | $1.0 \times 10^6$ |
| Glut:Carb c - 50 (40/10) | $1.4 \times 10^5$ | $<10^1$ | $<10^1$ |

TABLE 1B-continued

| Biocide (ppm a.i.) | 0 Hours | 4 Hours | 24 Hours |
| --- | --- | --- | --- |
| Glut:Carb c - 25 (20/5) | $1.4 \times 10^5$ | $<10^1$ | $<10^1$ |
| Glut:Carb c - 12.5 (10/2.5) | $1.3 \times 10^5$ | $<10^1$ | $1.5 \times 10^2$ |
| Glut:Carb c - 6.25 (5/1.25) | $1.0 \times 10^5$ | $1.0 \times 10^2$ | $2.2 \times 10^5$ |
| Glut:Carb d - 50 (40/10) | $9.0 \times 10^4$ | $<10^1$ | $<10^1$ |
| Glut:Carb d - 25 (20/5) | $1.3 \times 10^5$ | $<10^1$ | $<10^1$ |
| Glut:Carb d - 12.5 (10/2.5) | $1.1 \times 10^5$ | $<10^1$ | $2.3 \times 10^2$ |
| Glut:Carb d - 6.25 (5/1.25) | $2.0 \times 10^5$ | $1.2 \times 10^2$ | $2.3 \times 10^7$ |
| Control 0 | $8.8 \times 10^4$ | $8.5 \times 10^5$ | $4.2 \times 10^7$ |
| Control 0 | $1.2 \times 10^5$ | $5.3 \times 10^5$ | $3.8 \times 10^7$ |

EXAMPLE 3

A limited study using real mill furnish showed excellent efficacy of the Glutaraldehyde and the dithiocarbamate blend combination. The ratio investigated was a 4:1 Glutaraldehyde: Carbamate that theoretically uses the Glutaraldehyde to knock down the population initially and the Carbamate to hold it down. A mixture of 20 ppm Glutaraldehyde plus 5 ppm of carbamate gave comparable activity to 50 ppm of Glutaraldehyde alone. See Table 2.

TABLE 2

| | Glutaraldehyde:DTCB Testing | | | |
| --- | --- | --- | --- | --- |
| Biocide (ppm a.i.) | 0 Hours | 2 Hours | 6 Hours | 24 Hours |
| Glut - 100 | $8.0 \times 10^4$ | $2.4 \times 10^2$ | $1.4 \times 10^2$ | $2.4 \times 10^1$ |
| Glut - 50 | $2.0 \times 10^4$ | $4.2 \times 10^3$ | $2.0 \times 10^2$ | $7.0 \times 10^1$ |
| DTCB - 25 | $1.5 \times 10^7$ | $5.6 \times 10^6$ | $1.7 \times 10^3$ | $1.1 \times 10^3$ |
| DTCB - 12.5 | $1.3 \times 10^7$ | $5.2 \times 10^6$ | $1.0 \times 10^4$ | $4.3 \times 10^6$ |
| Glut:DTCB - 100 | $<10^3$ | $2.1 \times 10^2$ | $7.9 \times 10^1$ | $3.3 \times 10^1$ |
| Glut:DTCB - 50 | $1.7 \times 10^4$ | $3.1 \times 10^3$ | $2.0 \times 10^2$ | $7.0 \times 10^1$ |
| Glut:DTCB - 25 | $7.9 \times 10^5$ | $<10^3$ | $3.8 \times 10^2$ | $1.5 \times 10^2$ |
| Control - 0 | $9.6 \times 10^6$ | $2.3 \times 10^7$ | $1.9 \times 10^7$ | $3.3 \times 10^7$ |
| Control - 0 | $2.8 \times 10^7$ | $2.6 \times 10^7$ | $1.7 \times 10^7$ | $2.6 \times 10$ |

EXAMPLE 4

A 1st mill furnish, pH 7.8, gave excellent results with equal efficacy for the combination of Glutaraldehyde with the dithiocarbamate blend. With straight Glutaraldehyde counts were starting to increase after 24 hours while the counts for the combination were continuing to drop, although they did not drop as rapidly overall as the straight Glutaraldehyde. See attached data, Table #3. The abnormally low count for the 100 ppm concentration of Glutaraldehyde:Carbamate at 0 hour was shown to be an artifact due to a few minute delays in plating the sample.

TABLE 3

| | Glutaraldehyde:DTCB Combination | | | |
| --- | --- | --- | --- | --- |
| Biocide (ppm a.i.) | 0 Hour | 2 Hours | 6 Hours | 24 Hours |
| 1. Glut - 100 | $5.3 \times 10^6$ | $8.2 \times 10^1$ | $3.8 \times 10^1$ | $5 \times 10^0$ |
| 2. Glut - 50 | $1.4 \times 10^7$ | $7 \times 10^1$ | $5.4 \times 10^1$ | $9 \times 10^0$ |
| 3. Glut - 25 | $2.5 \times 10^7$ | $1.7 \times 10^2$ | $8 \times 10^1$ | $2.4 \times 10^1$ |
| 4. Glut - 12.5 | $3.8 \times 10^7$ | $3.7 \times 10^5$ | $8.9 \times 10^3$ | $1.9 \times 10^5$ |
| 5. DTCB - 20 | $3.5 \times 10^7$ | $3.3 \times 10^7$ | $8.2 \times 10^6$ | $9.1 \times 10^6$ |
| 6. DTCB - 10 | $4.5 \times 10^7$ | $5.1 \times 10^7$ | $2.3 \times 10^7$ | $2.7 \times 10^7$ |
| 7. DTCB - 5 | $3.3 \times 10^7$ | $6.2 \times 10^7$ | $2.4 \times 10^7$ | $3.5 \times 10^7$ |
| 8. DTCB - 2.5 | $3.9 \times 10^7$ | $7.0 \times 10^{19}$ | $6.9 \times 10^7$ | $4.1 \times 10^7$ |
| 9. G:DTCB(4:1) - 100 | $1.2 \times 10^2$ | $6.0 \times 10^1$ | $5.0 \times 10^1$ | $8 \times 10^0$ |
| 10. G:DTCB 50 | $2.0 \times 10^7$ | $5.0 \times 10^1$ | $1.0 \times 10^2$ | $2.8 \times 10^1$ |
| 11. G:DTCB 25 | $2.5 \times 10^7$ | $1.7 \times 10^7$ | $1.4 \times 10^2$ | $3.2 \times 10^1$ |
| 12. G:DTCB 12.5 | $2.7 \times 10^7$ | $1.2 \times 10^7$ | $2.4 \times 10^6$ | $1.9 \times 10^4$ |
| 13. Control - 0 | $5.3 \times 10^7$ | $2.8 \times 10^9$ | $1.8 \times 10^8$ | $1.6 \times 10^7$ |

TABLE 3-continued

| | Glutaraldehyde:DTCB Combination | | | |
| --- | --- | --- | --- | --- |
| Biocide (ppm a.i.) | 0 Hour | 2 Hours | 6 Hours | 24 Hours |
| 14. Control - 0 | $5.2 \times 10^7$ | $2.8 \times 10^9$ | $1.3 \times 10^3$ | $1.8 \times 10^7$ |

EXAMPLE 5

The Glutaraldehyde:the dithiocarbamate blend was run in two more mill furnishes. Definite synergy in the second system was seen for the combination in a newsprint furnish with the 25 ppm concentration giving better kill than straight Glutaraldehyde at all sample times. If synergy is calculated using $<10^1$ as the endpoint, a synergy index of 0.525 is achieved. See Table #4.

TABLE 4

| | Glut:DTCB (4:1) Combination Mill furnish, pH 4.9 | | | |
| --- | --- | --- | --- | --- |
| Biocide (ppm a.i.) | 0 Hour | 2 Hour | 6 Hour | 24 Hour |
| Glut - 100 | $1.5 \times 10^6$ | $<10^1$ | $<10^1$ | $<10^1$ |
| Glut - 50 | $5.1 \times 10^5$ | $2.2 \times 10^2$ | $<10^1$ | $<10^1$ |
| Glut - 25 | $3.0 \times 10^5$ | $2.1 \times 10^3$ | $6.8 \times 10^2$ | $<10^1$ |
| Glut - 12.5 | $5.2 \times 10^5$ | $2.1 \times 10^3$ | $2.6 \times 10^3$ | $5.2 \times 10^2$ |
| DTCB - 20 | $4.8 \times 10^5$ | $1.0 \times 10^3$ | $3.2 \times 10^2$ | $<10^1$ |
| DTCB - 10 | $1.4 \times 10^5$ | $1.5 \times 10^4$ | $3.8 \times 10^2$ | $2.8 \times 10^2$ |
| DTCB - 5 | $1.6 \times 10^5$ | $2.6 \times 10^4$ | $2.2 \times 10^3$ | $1.0 \times 10^5$ |
| DTCB - 2.5 | $1.5 \times 10^5$ | $1.3 \times 10^5$ | $4.8 \times 10^3$ | $2.1 \times 10^6$ |
| G:DTCB 4:1 - 100 | $2.8 \times 10^5$ | $<10^1$ | $<10^1$ | $<10^1$ |
| G:DTCB 4:1 - 50 | $2.4 \times 10^5$ | $<10^1$ | $<10^1$ | $<10^1$ |
| G:DTCB 4:1 - 25 | $1.2 \times 10^5$ | $2.9 \times 10^2$ | $<10^1$ | $<10^1$ |
| G:DTCB 4:1 - 12.5 | $1.3 \times 10^5$ | $4.6 \times 10^2$ | $1.2 \times 10^2$ | $<10^1$ |
| Control - 0 | $1.4 \times 10^5$ | $3.6 \times 10^5$ | $7.6 \times 10^5$ | $2.5 \times 10^6$ |
| Control - 0 | $1.3 \times 10^5$ | $5.5 \times 10^5$ | $1.6 \times 10^6$ | $2.7 \times 10^6$ |

Comments: Faster and more intense kill seen with the combination than with the straight biocides at all concentrations.

Results in the third furnish were not as good. Straight Glutaraldehyde outperformed the combination. Carbamate by itself looked poor in this furnish too. This appears to be the key to demonstrating synergy for the combination. If the carbamate is effective, then the combination has more of a chance to be synergistic.

I claim:

1. A method for controlling the microorganisms, *Pseudomonas aeruginosa* and spore forming bacteria, present in aqueous paper mill systems which comprises treating such systems with a biocidal amount of a composition comprising:
   a) Glutaraldehyde, and
   b) a biocidally active dithiocarbamate and mixtures thereof:
   with the weight ratio of a:b being greater that 1:10 but less than 15:1.

2. The method of claim 1 where the biocidally active dithiocarbamate and mixtures thereof are:
   a) Sodium dimethyldithiocarbamate
   b) Potassium dimethyldithiocarbamate
   c) Potassium-N-hydroxymethyl-N-methyl dithiocarbamate
   d) Potassium-N-methyldithiocarbamate, and

| e) Disodium ethlenebisdithiocarbamate | 50% by weight |
| --- | --- |
| Sodium dimethyldithiocarbamate | 50% by weight | with the weight ratio of a:b being from greater than 1:10 to 10:1.

3. The method of claim 1 where the weight ratio of a:b is 4:1 to 10:1.

* * * * *